(12) United States Patent
Whillock (10) Patent No.: US 8,677,542 B1
(45) Date of Patent: Mar. 25, 2014

(54) INTERCHANGEABLE TOOTH BRUSH SYSTEM AND ASSOCIATED METHOD FOR PROMOTING ORAL HEALTH

(71) Applicant: Edward B. Whillock, Rapid City, SD (US)

(72) Inventor: Edward B. Whillock, Rapid City, SD (US)

( * ) Notice: Subject to any disclaimer, the term of this patent is extended or adjusted under 35 U.S.C. 154(b) by 0 days.

(21) Appl. No.: 13/732,786

(22) Filed: Jan. 2, 2013

Related U.S. Application Data (63) Continuation of application No. 12/874,252, filed on Sep. 2, 2010, now abandoned.

(51) Int. Cl.
*A46B 9/04* (2006.01)

(52) U.S. Cl.
USPC .......................... 15/22.1; 15/DIG. 5; 15/167.1

(58) Field of Classification Search
USPC ............................ 15/21.1–22.2, 167.1, DIG. 5
See application file for complete search history.

(56) References Cited

U.S. PATENT DOCUMENTS

| | | | |
|---|---|---|---|
| 4,156,620 A | | 5/1979 | Clemens |
| 4,679,272 A | * | 7/1987 | Florence .......................... 15/106 |
| 4,845,795 A | * | 7/1989 | Crawford et al. ............... 15/22.1 |
| 5,165,761 A | | 11/1992 | Dirksing |
| 5,392,483 A | * | 2/1995 | Heinzelman et al. |
| 5,419,001 A | * | 5/1995 | Wan .............................. 15/167.1 |
| 5,435,034 A | | 7/1995 | Bigler et al. |
| 5,511,275 A | * | 4/1996 | Volpenhein et al. |
| 5,799,353 A | * | 9/1998 | Oishi et al. .................... 15/167.1 |
| 6,178,583 B1 | * | 1/2001 | Volpenhein |
| D454,251 S | * | 3/2002 | De Swarte et al. |
| 6,453,498 B1 | * | 9/2002 | Wu |
| 7,020,925 B1 | * | 4/2006 | Gitelis |
| 2003/0163881 A1 | * | 9/2003 | Driesen et al. ................. 15/22.1 |
| 2003/0196283 A1 | * | 10/2003 | Eliav et al. ..................... 15/22.1 |
| 2006/0000036 A1 | * | 1/2006 | Eliav et al. ..................... 15/22.1 |
| 2006/0037161 A1 | * | 2/2006 | Okada et al. .................. 15/167.1 |
| 2007/0233165 A1 | * | 10/2007 | Wagstaff ....................... 606/161 |
| 2008/0083077 A1 | * | 4/2008 | Alexander et al. ............. 15/53.1 |
| 2009/0029323 A1 | * | 1/2009 | Nejat ............................ 433/216 |
| 2010/0101038 A1 | * | 4/2010 | Garbers et al. ............... 15/167.1 |
| 2010/0115725 A1 | * | 5/2010 | Kwon et al. .................. 15/167.1 |

OTHER PUBLICATIONS

Matilla KJ, Nieminen MS, Valtonen VV, et al. Association between dental health and acute myocardial infarction BMJ 1989;298:779-781.*

DeStefano F, Anda RF, Kahn HS, Williamson DF, Russell CM. Dental disease and risk of coronary heart disease and mortality. BMJ 1993;306:688-691.*

(Continued)

*Primary Examiner* — Laura C Guidotti
(74) *Attorney, Agent, or Firm* — M. Paul Hendrickson; Ashkan Najafi (57) ABSTRACT

An improved antimicrobial electric toothbrush and method includes a handle, a tip, and a plurality of bristle tufts and a drive mechanism. The bristle tufts may include four tufts of 10.5 mm length and another four tufts of 5.5 mm length. The tips of the bristle tufts may additionally be spaced apart and includes a cone shaped tip. The size and diameters of the bristle tufts may be combined with the reciprocating movement of the bristle tufts such that the bristle tips can reach into the crevices and tight spaces between the teeth and between the teeth and gums where no conventional toothbrush can reach. A second component of the apparatus may include an improved brush design with two counter rotating arrays of bristle tufts for use in polishing the teeth.

20 Claims, 7 Drawing Sheets

(56) References Cited

OTHER PUBLICATIONS

Offenbacher S, Katz V, Fertik G, et al. Periodontal infection as a possible risk factor for preterm low birth weight. J Periodontol 1996;67(10 Suppl.):1103-1113.*

Beck J, Garcia R, Heiss G, Vokonas PS, Offenbacher S. Periodontal disease and cardiovascular disease. J Periodontol 1996;67 (10 Suppl.):1123-1137.*

Barrett MJ, The oral-systemic disease connection. An update for the practicing dentist. J Am Dent Assoc 2006; 137:5S-6S.*

Loe H, Theilade E, Jensen SB. Experimental gingivitis in man. J Periodontol 1965;36:177-87.*

Brandtzaeg P, Jamison HC. The effect of controlled cleansing of the teeth on periodontal health and oral hygiene in Norwegian army recruits. J Periodontol 1964;35:308-12.*

Suomi JD, Greene JC, Vermillion JR, Doyle J, Chang JJ, Leatherwood EC. The effect of controlled oral hygiene procedures on the progression of periodontal disease in adults.*

Lightner LM, O'Leary TJ, Drake RB, Crump PP. Allen MF. Preventive periodontic treatment procedures: results over 46 months. J Periodontol 1971;42(9):555-61.*

Axelsson P, Nystrom B, Lindhe J. The long term effect of a plaque control program on tooth mortality, caries and periodontal disease in adults: results after 30 years of . . . .*

Morris AJ, Steele J, White DA. The oral cleanliness and periodontal health of UK adults in 1998. Br Dent J 2001;191(4):186-92.*

Williams K, Ferrante A, Dockter K, Haun J, Biesbrock AR, Bartizek RD. One and three minute plaque removal by a battery-powered versus manual toothbrush. J Periodntol 2004;75.*

Segelnick SL. A survey of floss frequency, habit and technique in a hospital dental clinic and private periodontal practice. NY State Dent J 2004;70(5):28-33.*

American Dental Association. 2003 public opinion survey: Oral health of the US population. Chicago:American Dental Association;2004.*

Backdash B. Current patterns of oral hygiene product use and practices. Periodontol 2000 1995;8:11-4.*

* cited by examiner

INTERCHANGEABLE TOOTH BRUSH SYSTEM AND ASSOCIATED METHOD FOR PROMOTING ORAL HEALTH

CROSS REFERENCE TO RELATED APPLICATIONS

This application is a continuation application of U.S. patent application Ser. No. 12/874,252 filed Sep. 2, 2010, currently pending, which claims the benefit of U.S. Provisional Application No. 61/258,430, filed Nov. 5, 2009 now abandoned, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION
TECHNICAL FIELD

This invention relates to dental healthcare and, more particularly, to an easy to use and highly effective system and method of personal oral hygiene. It includes an antimicrobial electric oral hygiene brush with an improved bristle tuft design and configuration. This brush not only cleans the easily accessed surfaces of the teeth similar to conventional toothbrushes; the bristle tips are capable of reaching into subgingival and interproximal areas where conventional toothbrushes and dental floss cannot reach. It is used with antimicrobial agents and NOT conventional toothpaste.

PRIOR ART

Dental Diseases are a Universal Problem:

Few humans throughout the world escape the consequences of dental caries, gingivitis or periodontal diseases. Even people who take care of their teeth faithfully, using procedures recommended by dentists, continue to have tooth decay, gingivitis or periodontal diseases. Using fluoride toothpaste regularly, having fluoridated water, and daily flossing help to a degree, but do not guarantee periodontal health or eliminate tooth decay for most people. A major reason for the relative failure of conventional mouth care is that these measures fail to remove disease-causing bacteria from between the teeth and from below the edge of the gum where the gum contacts the surface of the tooth.

Periodontal Disease Linked to Other Diseases:

It is now widely recognized that periodontal diseases contribute to other systemic diseases including coronary heart disease, stroke, premature low birth weight babies and other diseases. (See citations numbers 1-6 on applicant's Invention Disclosure Statement).

The bacteria that grow in the mouth, flourishes along the gum line, in the small seams and gaps between the teeth, and between the teeth and gums. Conventional oral hygiene does not get rid of most of these bacteria even though all the usual procedures of brushing correctly and flossing daily or even more often are carried out. Neither conventional toothbrushes nor dental floss are capable of reaching bacteria deeper than a millimeter or two below the edge of the gum. It is generally recognized that conventional toothbrushes cannot reach between the teeth; for this reason, dental floss is advocated to clean these areas.

Effective Prevention is Possible:

It has been shown that adequate control of bacterial plaque biofilm can reverse the development of gingivitis. (See citation number 7 on applicant's Invention Disclosure Statement). It is generally accepted that adequate control of oral bacterial biofilm is an effective way to prevent dental caries, gingivitis and periodontal diseases. Several clinical trials have shown that rigorous levels of bacterial biofilm control is effective in preventing the onset or controlling the progression of caries and periodontal diseases over extended time periods. (See citations numbers 8-10 on applicant's Invention Disclosure Statement). Axelsson, Nystrom and Lindhe showed that meticulous oral biofilm control was effective in preventing dental caries and periodontal disease in a patient cohort for thirty years. (See citation number 11 on applicant's Invention Disclosure Statement). These successes have occurred in carefully controlled circumstances and serve as "proof of concept" that keeping commonly occurring pathogenic bacteria from populating the mouth is an effective way to prevent dental caries, gingivitis and periodontal diseases.

Current Devices Inadequate:

However, there are real life limitations to the effectiveness of mechanical and antimicrobial methods of oral bacterial biofilm control with the devices available in the market place at this time. Most people are unable to remove the oral bacterial biofilm from the difficult to reach areas well enough to achieve the level of oral health maintained in the studies referenced above. Several published reports and most people's personal experience with having dental diseases themselves, illustrate the inadequacy of the currently available oral hygiene devices. For example, Morris and colleagues found that 72 percent of all the dentate adults examined were found to have visible plaque. (See citation number 12 on applicant's Invention Disclosure Statement). A study by Williams and colleagues found that brushing with a powered toothbrush resulted in reductions of oral plaque biofilm of only 20 and 31 percent after one and three minutes of brushing respectively. (See citation number 13 on applicant's Invention Disclosure Statement). Surveys to investigate the flossing habits and use of interdental cleaning devices indicate that people in the studied populations used these devices on a daily basis between 11 and 51 percent of the time. (See citation numbers 14-16 on applicant's Invention Disclosure Statement). These studies and many others illustrate the difficulty of accomplishing adequate oral biofilm control with the devices available today.

Why Current Devices Fail:

There are several reasons that conventional toothbrushes, dental floss and mouth rinses fail to enable most people to maintain a completely healthy mouth. For example, the toothbrushes available today are incapable of reaching into all of the areas of the mouth that are occupied by oral bacterial biofilm. Many people do not brush thoroughly enough to remove the oral biofilm from the areas in which the biofilm bacteria reside. Most people brush their teeth to remove food debris and to polish or remove stains, not to remove microbial masses from the more difficult-to-reach areas these microbes inhabit. Dental floss is difficult for most people to use. Therefore most people do not use it. It is impossible for some people to use effectively due to limited manual dexterity or conditions in their mouths. Many of the people who do use floss are ineffective with it because it is technically difficult to use correctly.

Dental floss, when used properly, does remove bacterial communities from the flat and convex interproximal tooth surfaces, but it does not reach into concave areas. Dental floss does not kill significant numbers of bacteria. Dental floss takes time to use properly. Many people are not willing to take the extra time required to use it.

Mouth rinses have been shown to reduce supragingival plaque and gingivitis. However, the slime that is produced by the oral bacteria forms a barrier that mouth rinses do not penetrate. Therefore, the antimicrobial effect of the mouth rinse is limited. Mouth rinse does not kill the majority of the bacteria living within the biofilm community. This has been verified many times clinically by having people rinse with an antimicrobial mouth rinse for two minutes or more.

After the rinsing is complete, visual examination reveals that very little of the oral biofilm has been removed by the rinsing. Samples of the oral biofilm material that was not removed by the rinsing activity are collected from the person's mouth, placed on a microscope slide, magnified through a phase contrast microscope and viewed on a video display. The motile bacteria contained in the biofilm samples are seen to be swimming and moving around similar to those seen in the samples collected from the person's mouth prior to doing the rinsing procedure. This verifies that the bacteria living in the biofilm community are not removed from the mouth or killed by rinsing with an antimicrobial mouth rinse.

The slime produced by the oral bacteria biofilm clings to the tooth surface so tenaciously that even biofilm located on facial or lingual surfaces of the teeth where the mouth rinse comes into direct contact with the biofilm, remains after the rinsing exercise.

Swishing and rinsing with a mouth rinse does not force it into the subgingival areas. Therefore, there is little or no beneficial effect in these areas. Its antimicrobial effect is mostly limited to supragingival bacteria and bacteria that reside on the mucosal surfaces that are not protected by the slime surrounding the biofilm community.

Swishing and rinsing with an antimicrobial mouth rinse after brushing and flossing may remove bacteria that have been dislodged from the tooth surfaces by the conventional brushing and flossing. However, it does not affect the dental plaque biofilm in the gingival sulcus and the interproximal areas that were not reached by the action of the conventional brush and floss.

Re-Educating the Public:

The public in general, continues to believe dental diseases are linked to food debris that remains on the teeth after eating. Showing people the swarms of living, swimming bacteria contained within the oral plaque biofilm, (magnified by a phase contrast microscope and viewed on a video display) and where it came from, helps them realize what is left behind by conventional brushing, flossing and rinsing. They begin to understand why they continue to have dental diseases and that a new approach to oral hygiene is required to prevent or stop the dental diseases in their mouths. They begin to see how these bacteria can enter the bloodstream and can spread to other parts of the body and may be involved in causing or contributing to other diseases in the body.

Showing people who have learned about the bacteria that are actively growing and swimming around their teeth and gums, the capabilities of the bristle action of this invention and its method of use, provides encouragement and motivation for them. They can see how easy this invention is to use and that adopting this method of use can help to eliminate or greatly reduce their dental disease problems. They are usually eager to begin using this new method of mouth care and ask where they can get the items they need to get started.

This Invention Satisfies the Need:

Accordingly, a need remains for an oral health brush and mouth-care system in order to overcome the above-noted shortcomings. The present invention satisfies such a need by providing a toothbrush kit including interchangeable antimicrobial and polishing brush heads that are convenient and easy to use, lightweight yet durable in design, versatile in their applications, and designed for providing users with an improved means for removing antimicrobial masses from between the teeth and under the edges of the gums (subgingival areas) that cannot be reached using a normal toothbrush and dental floss.

BRIEF SUMMARY OF THE INVENTION

An important advantage of this system is that the bristle design and action of the bristles, delivers antimicrobial agents (preferably in a convenient "liquigel" form) into these difficult-to-access areas at the same time the bristle action disrupts the oral plaque biofilm. The bristle action disrupts the slime layer of the oral plaque biofilm that normally protects the microbes living within the biofilm, from being killed by mouth rinses, antibiotics and the like. The sticky nature of the slime also prevents mouth rinses from removing the biofilm bacteria from tooth surfaces during rinsing. This combination mechanical and antimicrobial action reduces the dental plaque biofilm remaining in the mouth after cleaning to a small fraction of what remains after conventional brushing, flossing and rinsing. This results in a much lower survival of viable bacteria to begin recolonizing the oral cavity and a much healthier mouth.

An important advantage of using this system and method of oral hygiene is that it is simple and efficient to use. Virtually all of the tooth surfaces, the interproximal and subgingival areas and the dorsal surface of the tongue can be cleaned and treated with an antimicrobial agent in 2 to 2½ minutes.

Patients who have previously had significant tooth decay and gum diseases throughout their lives have had their mouths remain disease-free while they have tested and used this system regularly and thoroughly. This system and method introduces a new paradigm for personal oral hygiene that is much easier to perform and much more effective than the current standard of care that consists of brushing, flossing and rinsing.

This system and method of use is a much needed advancement in the art and science of preventing oral diseases and diseases in other parts of the body that may be linked to oral diseases. Proper use of this system can significantly reduce the incidence of these diseases. The cost of treatment of these diseases can be greatly reduced. In this time of concern for the escalating healthcare costs, introduction of this system and method of mouth care to the public can provide substantial relief from these escalating costs in money and in the loss of individual and public well being. The public can now have a device and method of use that is more effective and easier to use than conventional toothbrushes and dental floss.

This system and method also includes a second interchangeable brush head that gently and effectively polishes teeth. The brush head consists of two counter rotating arrays of bristle tufts. This brush is to be used with a polishing/whitening cream rather than toothpastes that are often abrasive to exposed tooth root surfaces. Use of this brush head will replace the horizontal scrubbing action that most people use while brushing their posterior teeth with toothpaste. The result will be a significant reduction in the incidence of so called toothbrush abrasion on exposed tooth root surfaces.

The invention and method of use overcomes the deficiencies of the currently available manual and electric toothbrushes and dental floss. The shape, configuration and the action of the bristle tips make it possible for the bristle tips to enter into subgingival areas, interproximal areas and concavities that conventional toothbrushes and dental floss cannot reach. Because the brush is used with antimicrobial agents rather than conventional toothpastes, this oral hygiene system and method is capable of killing and removing a very large percentage of the oral bacterial biofilm with each use. The unprecedented ability of this system to kill and remove bacteria from the many creases, crevices and grooves formed by the anatomy the teeth and gums can reduce the numbers of bacteria to well below the threshold necessary to cause disease. This system and method of use greatly enhances the effect of antimicrobial mouthwashes. The preferred embodiment of this system uses an antimicrobial agent in a more viscous "liquigel" form because it is easier to keep in the mouth while using the brush.

The antimicrobial brush head is used only with antimicrobial agents and not conventional toothpastes. This is because the polishing grit contained in toothpastes gets into the gears that drive the bristle tufts and creates so much friction that the reciprocating, counter-rotating bristle tuft action can be stopped. In addition, if toothpaste is allowed to dry in the gears and drive mechanism, the brush head becomes inoperable.

In view of the foregoing background, it is therefore an object of the present invention to provide an oral health brush and mouth-care system that has the following traits: an easy-grip handle, a motor drive system, an antimicrobial brush head, a polishing brush head, a unique bristle tuft design, an antimicrobial liquid-gel that acts as a germ-killing agent (liquigel or mouthwash), that kills and removes bacteria from areas under the edges of the gums (subgingival) and between the teeth where other oral-hygiene devices cannot reach.

It is another object of the present invention to provide a more effective and efficient way to maintain optimal mouth health at home compared to conventional methods of brushing and flossing. The system uses a unique antimicrobial brush-head that works in conjunction with an antimicrobial liquigel.

It is a further object of the present invention, to keep the mouth healthy and teeth polished and thereby helps prevent tooth decay and gum disease, and decrease the risk of heart disease, stroke and other medical conditions associated with periodontal disease.

It is a further object of the present invention to provide an effective tooth polishing system that uses a unique polishing brush-head that works in conjunction with polishing/whitening cream.

It is a further object of the present invention, to reduce the time necessary to keep mouth disease-free. Flossing takes extra time, does not kill bacteria, nor does it reach the bacteria living in the majority of the crevices in the gums.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

Those skilled in the art will appreciate that the figures are not intended to illustrate every embodiment of the invention.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the true spirit and scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "present invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. §1.72(b) and is submitted with the understanding that it will not be used to interpret or limit the scope or meaning of the claims. In addition, in the foregoing detailed description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the detailed description, with each claim standing on its own as defining separately claimed subject matter.

The below disclosed subject matter is to be considered illustrative, and not restrictive, and the appended claims are intended to cover all such modifications, enhancements, and other embodiments which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

The toothbrush of this invention is referred to generally in FIGS. 1-9 by the reference numeral 10 and is intended to provide an oral health toothbrush that has a handle 11 for selectively receiving an interchangeable antimicrobial brush head 30 intended for use with an antimicrobial liquigel 35 and an interchangeable polishing brush head 60 intended to be used with a polishing/whitening cream 65.

It should be understood that the present disclosure may be referred to collectively as a system or kit that includes toothbrush 11, brush heads 30, 60, antimicrobial liquigel 35 and/or polishing/whitening cream 65 for removing antimicrobial masses from between the teeth and under the edges of the gums (subgingival) that cannot be reached using a normal toothbrush and the like. The toothbrush may be power-operated via an electric motor 52.

Referring to FIGS. 3-6 and 9, the electric motor 52 may operate a rotary drive mechanism 50 that causes adjacent 31, 32 bristle tufts to twist in opposite directions as the bristle tuft action reciprocates back and forth in clockwise and counter clockwise directions. Such opposite rotary motions are further explained hereinbelow. The unique configuration and spatial relationship of the 31, 32 bristle tufts allows them to deliver antimicrobial agents into areas between teeth, and into the areas between gums and teeth (subgingival). Additionally, the motor drive mechanism (collectively referred to at 50, 52) may feature a timer (as part of drive mechanism 50) to guide the user in doing a thorough removal of microbial biofilm from the crevices and grooves between the teeth and between the teeth and gums. Of course, one skilled in the art understands the timer may be a separate timer circuit/switch that is electrically coupled to the motor drive mechanism 50. The electric motor may also operate a drive mechanism that causes the adjacent bristle tuft arrays 63, 64 of the polishing brush head to turn continuously in opposite directions.

Figure 9:
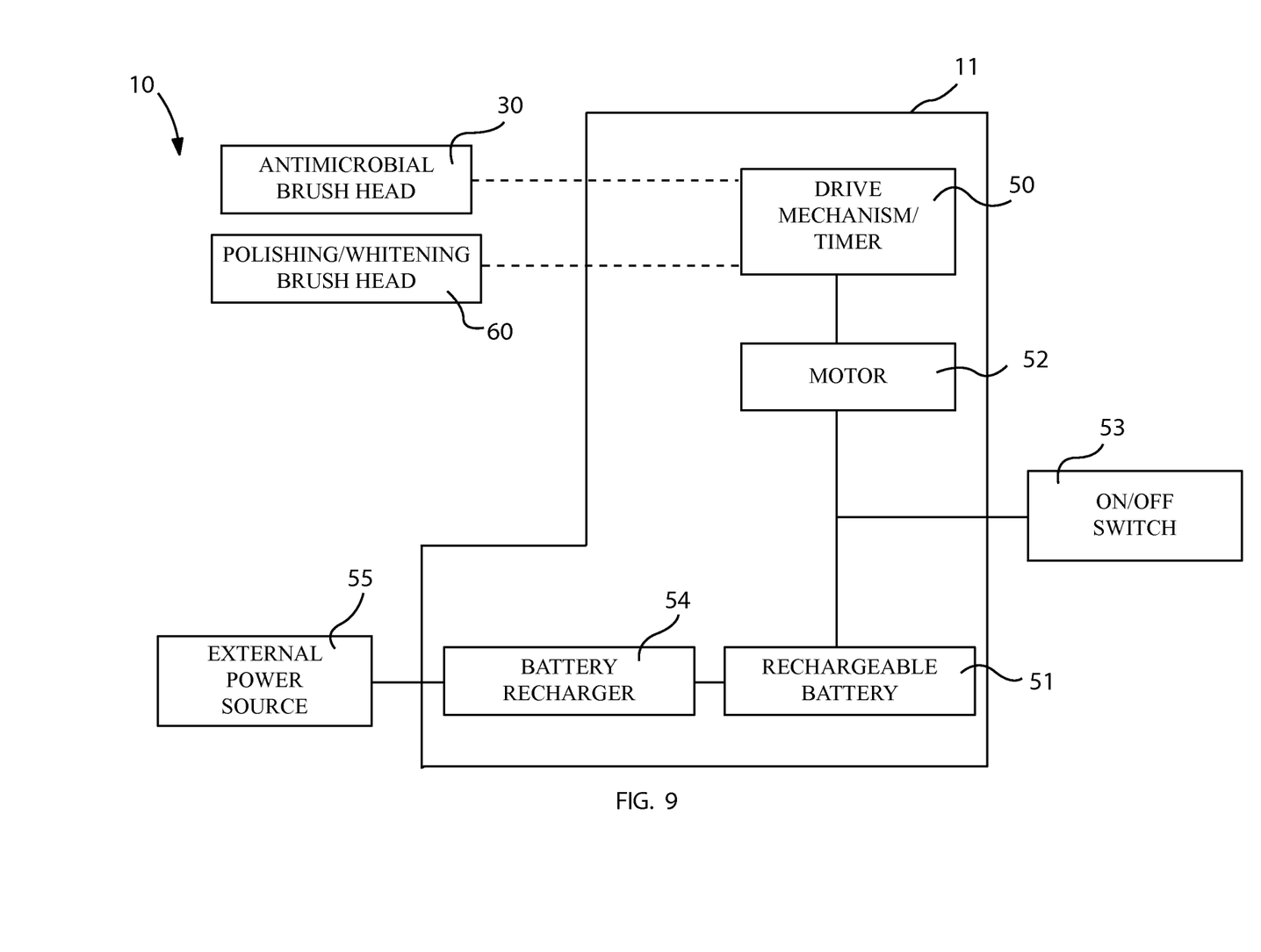
FIG. 9 is an exemplary embodiment of a high-level schematic block diagram showing the interrelationship between the major electronic components of the toothbrush.

As perhaps best shown in FIG. 9, it is noted that a variety of conventional motor drive mechanisms may be employed by the toothbrush 11. One skilled in the art understands that rotary motor drive mechanism 50, 52 is merely one example of suitable motor drive mechanisms that may be employed by the toothbrush 11. Alternate motor drive mechanisms may be employed without departing from the true spirit and scope of the present invention. As an example, the motor drive mechanism 50, 52 may be powered by a rechargeable internal battery 51 and/or an external power source 55. A battery recharger 54 may be included for recharging the battery 51 periodically when connected to power source 55. A user interface 53, such as an on/off switch, may be electrically coupled to battery 51 and motor drive mechanism 50, 52, for operating the toothbrush 11.

Figure 1:
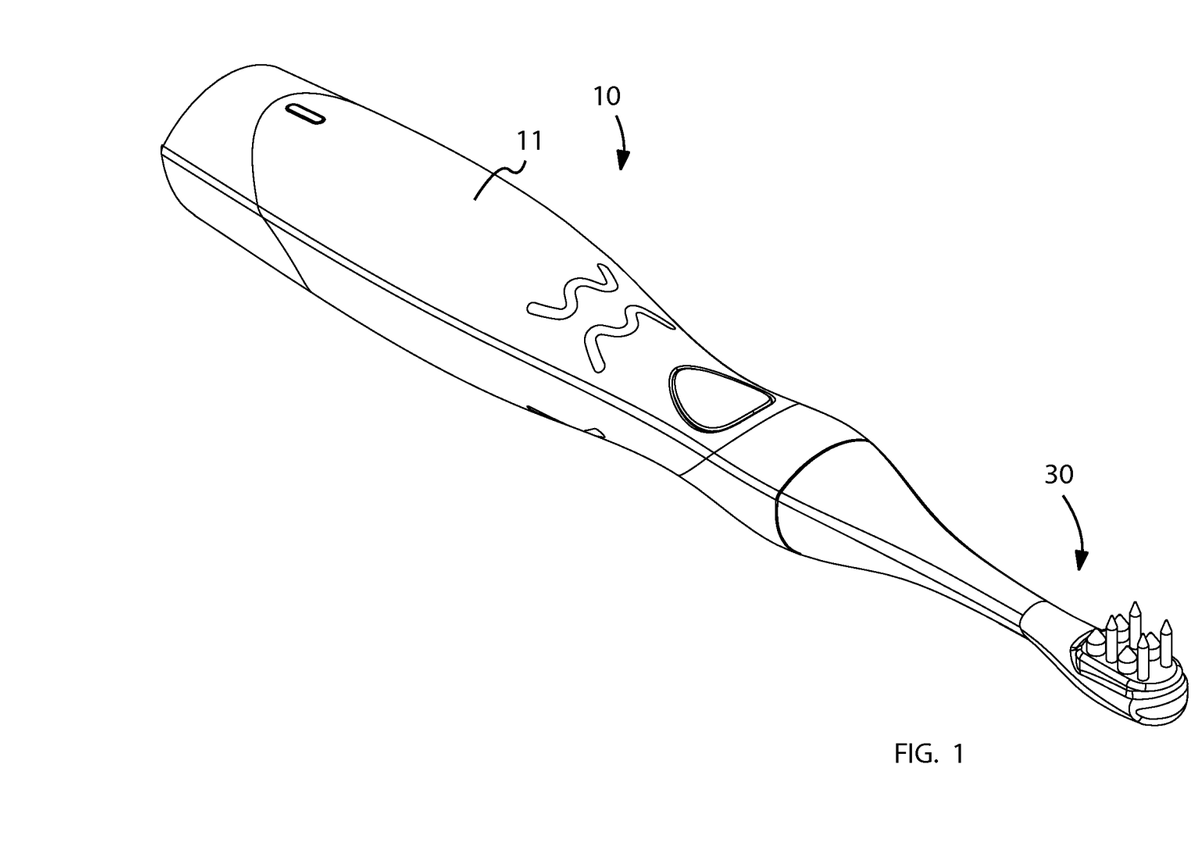
FIG. 1 is a perspective view showing a toothbrush employing an interchangeable antimicrobial brush head, in accordance with the present invention.
Figure 2:
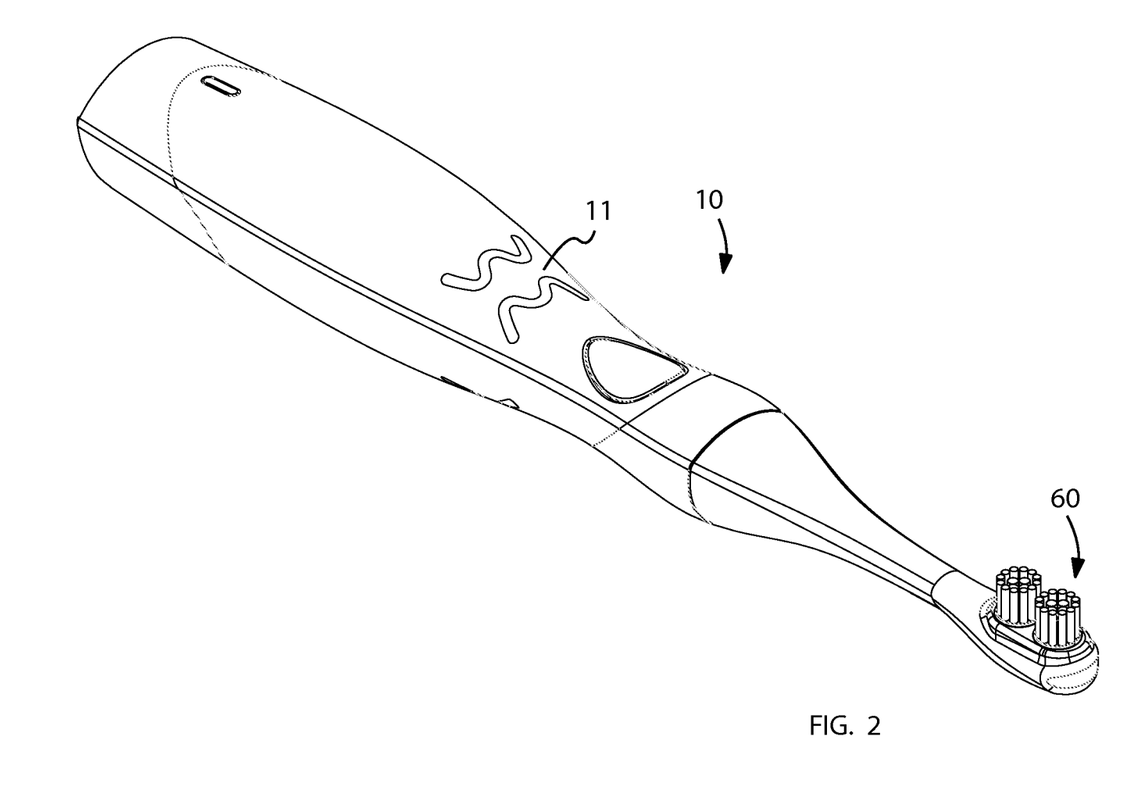
FIG. 2 is a perspective view showing a toothbrush employing an interchangeable polishing/whitening brush head.

Referring generally to FIGS. 1-2, the oral health brush and mouth-care system preferably includes toothbrush 10 having handle 11, a plurality of interchangeable brush heads 30, 60. Each brush head 30, 60 preferably has a plurality of first 31, 32 and second 63, 64 bristle tufts respectively arranged in a predetermined configuration which is critical for performing the intended antimicrobial/polishing functions described hereinbelow.

There are several advantages in the structure and function of brush heads 30, 60 and prior art brush heads. Initially, antimicrobial brush head 30 is not specifically intended to be a toothbrush per se. It is intended to be an antimicrobial toothbrush. In addition to cleaning the teeth, the bristles of the antimicrobial brush head 30 clean areas between the teeth and under the edges of gums (subgingival) that are not accessible with conventional toothbrushes. It is noted that conventional toothbrushes are designed to primarily clean and polish exposed enamel surfaces of the teeth with only toothpaste. In addition, conventional toothbrush bristles are spaced too close together and/or have a drive mechanism that does not enable the bristle tips to enter spaces between the teeth and under the edges of gums (subgingival areas between the gum and the tooth). The antimicrobial brush head 30 has an advantageous configuration of first bristle tufts 31, 32 that effectively accesses areas between the teeth and the gums (subgingival) where conventional brushes cannot.

The uniquely shaped first bristle tufts 31, 32 of antimicrobial brush head 30 advantageously carries antimicrobial agents (from liquigel 35) into these previously unreachable subgingival areas to provide a combination of a scrubbing action thereby dislodging bacterial masses from soft tissues and tooth surfaces and exposing the bacteria to the killing effects of the antimicrobial agent. Thus, this structural configuration of first bristle tufts 31, 32 advantageously disrupts the protective slime layer and enables the antimicrobial agent to kill the bacteria that live there. Simply swishing a mouthwash in the mouth does not remove the bacteria living in the slime-protected colonies on the tooth surfaces, from between the teeth or the subgingival areas. This has been verified many times by having a patient swish a mouthwash in his or her mouth for two minutes or more only to find living motile bacteria in these areas after they finished the swishing exercise. The fact that the remaining bacteria are still alive is verified via microscopic examination of the material collected from a person's mouth after two or more minutes of swishing.

The number of bacteria that survive after mouth cleaning with the antimicrobial brush head 30 and antimicrobial liquigel 35, is miniscule compared to the bacteria that survive after mouth cleaning with conventional tooth brushing, flossing and mouthwash rinsing procedures. Further, the antimicrobial brush head 30 is preferably not intended to be used with toothpaste because the polishing grit in the toothpaste may get into the gears of antimicrobial brush head 30. This may cause friction in the gears, thereby causing bristle tufts 31, 32 to stop moving. Therefore, the antimicrobial brush head 30 should be used with the antimicrobial liquigel 35 or antimicrobial mouthwash.

First Brush Head (Antimicrobial Brush Head)

Figure 3:
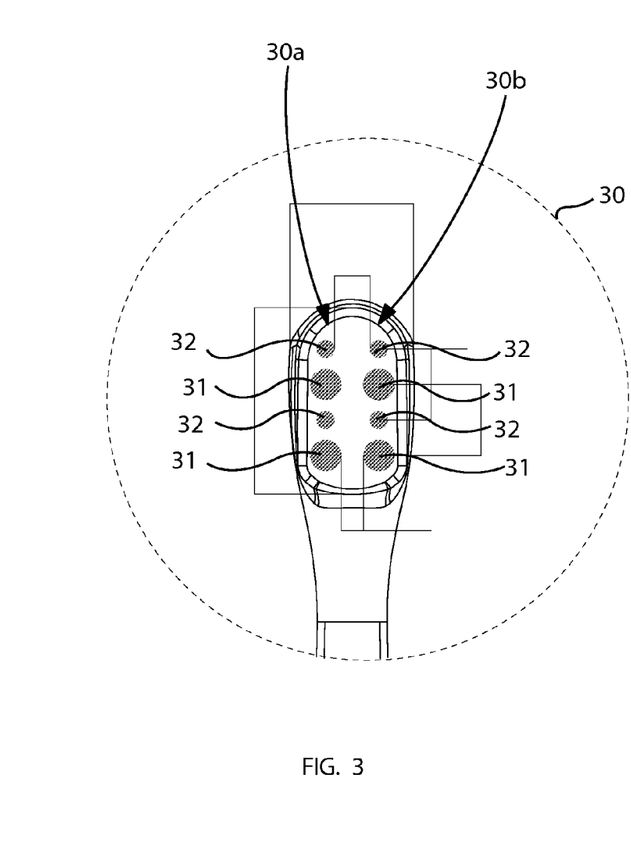
FIG. 3 is an enlarged top plan view showing the configuration and spatial relationship between the bristle tufts of the antimicrobial brush head.
Figure 4:
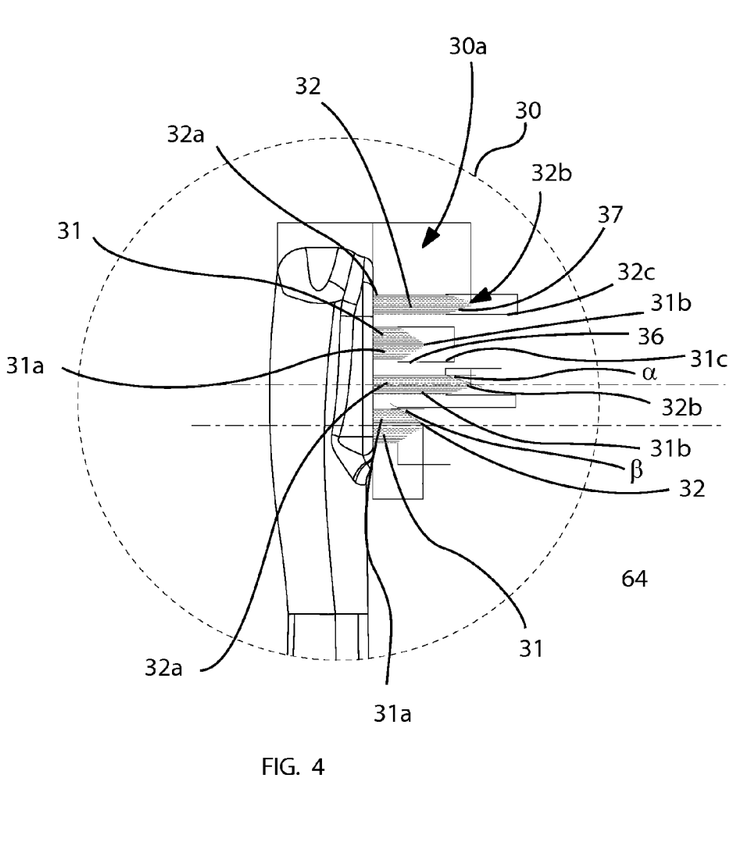
FIG. 4 is side elevational view of FIG. 3.

Referring to FIGS. 1, 3 and 4, an exemplary embodiment of the present disclosure, illustrates an antimicrobial brush head 30 blue in color to coordinate with the blue color of the antimicrobial liquigel 35, preferably including eight first bristle tufts 31, 32 arranged in first and second linear rows 30*a*, 30*b* extending along left and right sides of brush head 30. In particular, each row 30*a*, 30*b* preferably has two short bristle tufts 31 and two long bristle tufts 32 arranged in an alternating pattern. The short and long first bristle tufts 31, 32 have different heights, as described hereinbelow. Filaments of the long bristle tufts 32 are slightly stiffer (0.007 inch in diameter) than conventional brushes so they can effectively enter crevices between teeth. Filaments in short bristle tufts 31 are preferably softer (0.004 inch in diameter) than long bristle tufts 32 to gently clean crevices along the buccal and lingual surfaces of the teeth.

Referring to FIGS. 3-4, and 9-10 as a non-limiting example, each of the long 32 and short 31 bristle tufts are driven by a drive mechanism 50 and motor 52 that may include a conventional rack and gear system 50 (depicted in FIG. 10) that causes the individual long 32 and short 31 bristle tufts to selectively rotate in opposite directions as they reverse directions. One skilled in the art understands such opposite rotational movements of each of the long 32 and short 31 bristle tufts may be achieved by abutting two rotary gears 50S and 50L wherein clockwise rotation of one rotary gear 50S causes counter clockwise rotation of the other rotary gear 50L. As an example, the short first bristle tufts 31, of the antimicrobial brush head may rotate 1.25 turns clockwise then reverse direction and twist counter clockwise 1.25 turns while the long first bristle tufts 32 rotate 1.25 turns counter clockwise then reverse direction and twists clockwise 1.25 turns. Such a drive mechanism 50, may encompass a variety of alternate configurations and components and should not be limited to only rotary gear configurations.

Figure 7:
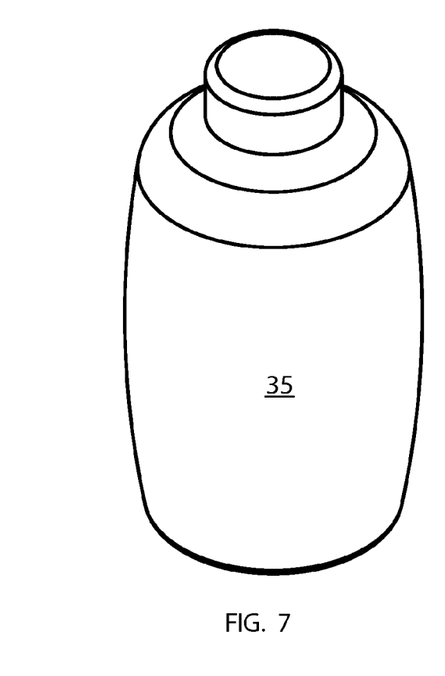
FIG. 7 is a perspective view showing the antimicrobial liquigel that serves as a germ-killing agent.
Figure 8:
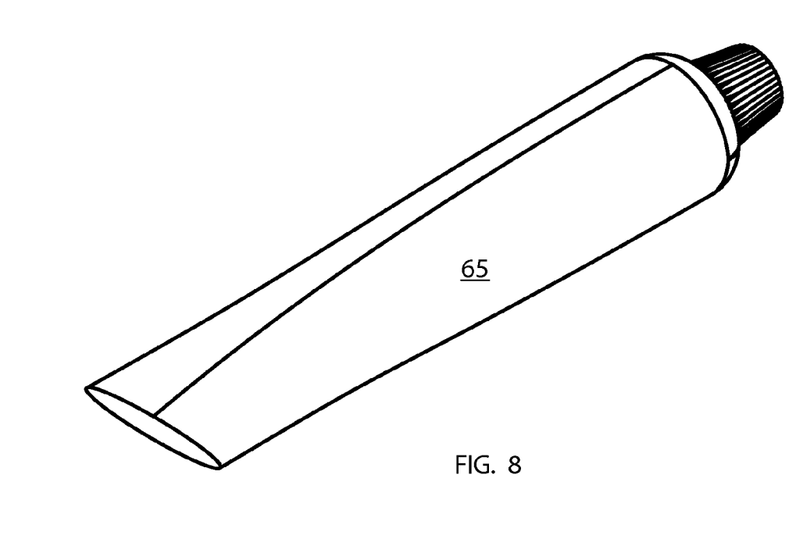
FIG. 8 is a perspective view showing the polishing/whitening cream.

As perhaps best shown in FIG. 7, the antimicrobial liquigel 35 may be housed in a bottle. Such a liquigel 35 preferably incorporates a germ-killing agent that when used with antimicrobial brush head 30 kills and removes bacteria living in these critical areas of the mouth (such as subgingival areas). Gel-like liquid is easier to retain in the mouth during brushing than conventional mouthwashes. Toothpastes should not be used because the polishing grit (or crystals) in them get into the fine gears of the brush head and block the rotating of the first bristle tufts 31, 32 over a short period of use. Thus, liquigel 35 ensures longevity of the antimicrobial brush head 30.

Referring to FIGS. 3-4, the configuration of the shape, length, stiffness, spacing and action of first bristle tufts 31, 32 for antimicrobial brush head 30 may be as follows: the antimicrobial brush head 30 may preferably have two rows 30*a*, 30*b* of four first bristle tufts 31, 32 with approximately three to four millimeters of spacing between the two rows 30*a*, 30*b* of first bristle tufts 31, 32. The final dimension may further be determined by the size of drive mechanism 50 components located in the antimicrobial brush head 30.

There are four longer bristle tufts 32 that are preferably approximately 10.5 millimeters in longitudinal length. The diameter of such longer bristle tufts 32 may be approximately two millimeters at their base (proximal end) 32*a*. The individual filaments of the longer bristle tufts 32 may have slightly larger diameters (0.007 inch in diameter), than the diameter of the short bristle tuft 31 filaments, to provide slightly stiffer bristle tufts. Advantageously, the structural dimensions of long bristle tufts 32 permit reach and access into the spaces between the teeth and between the gum and tooth (subgingival) in interproximal areas.

Still referring to FIGS. 3-4, shorter bristle tufts 31 are preferably approximately 5.5 millimeters in longitudinal length. Filaments of the short bristle tufts 31 may be slightly smaller in diameter (0.004 inch in diameter), than the diameter of the long bristle tuft 32 filaments, and softer in texture than the filaments of the long bristle tufts 32. The diameter of the short bristle tufts 31 may be approximately 3.5 millimeters at the base (proximal end) 31*a*, for example.

As perhaps best shown in FIG. 4, both long bristle tufts 32 and short bristle tufts 31 preferably have tapered distal ends 32*b*, 31*b*. For example, the distal 2.5 millimeters of first bristle tufts 31, 32 may be tapered to a substantially cone shape such that the angle "$\alpha$" 37 of the cone shaped distal ends 32*b* may be about 21.8 degrees measured from a longitudinal axis 32*c* of the long bristle tufts 32. The angle "$\beta$" 36 of the cone shaped distal end 31*b* of the short bristle tufts 31 may be about 35 degrees measured from a longitudinal axis 31*c*. The advantage of such a structural configuration allows the tips (apex of distal ends 31*b*, 32*b*) of short and long first bristle tufts 31, 32 to reach under the edges of the gum between the gum and the tooth (subgingival area) along the sides of the teeth.

As perhaps best shown in FIG. 4, the respective spatial distances between corresponding tips (apex of distal ends 31*b*, 32*b*) of short and long first bristle tufts 31, 32 may be approximately 8 millimeters. Such a spatial relationship advantageously allows the tips of the long first bristle tufts 32, to reach into areas between the teeth and the short bristle tufts 31 to reach into the subgingival areas on the buccal and lingual surfaces of the teeth.

Second Brush Head (Polishing Brush Head)

Referring to FIGS. 2, 5-6 and 8-9, the second brush head 60 may be a polishing brush head interchangeably attached to handle 11 of toothbrush 10 and preferably operates using motor drive mechanism 50, 52. As an example, such a polishing brush head 60 may be white in color and thereby coordinate with the white polishing/whitening cream 65. The white color helps distinguish the polishing brush head 60 from the blue antimicrobial brush head 30. Polishing/whitening cream 65 is used in conjunction with the polishing brush head 60 to help remove stains from the teeth.

Figure 5:
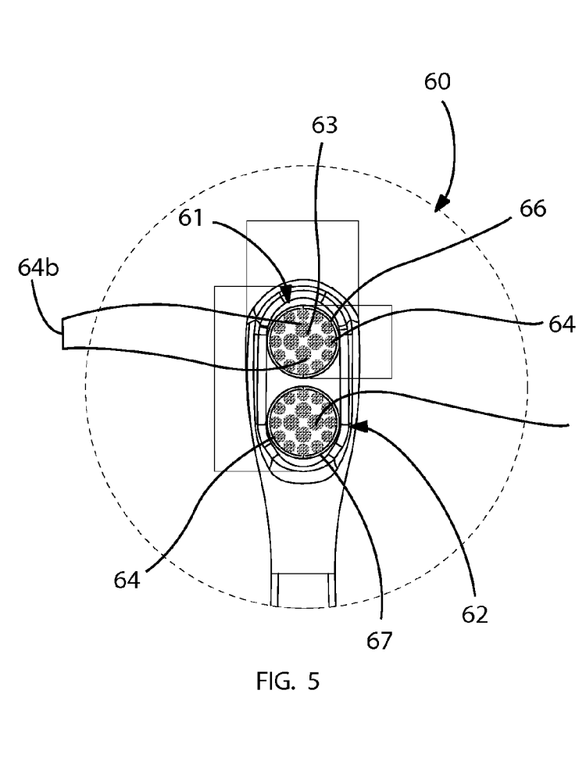
FIG. 5 is an enlarged top plan view showing the configuration and spatial relationship between the first and second bristle tufts arrays as well as their respective bristle tufts of the polishing brush head.
Figure 6:
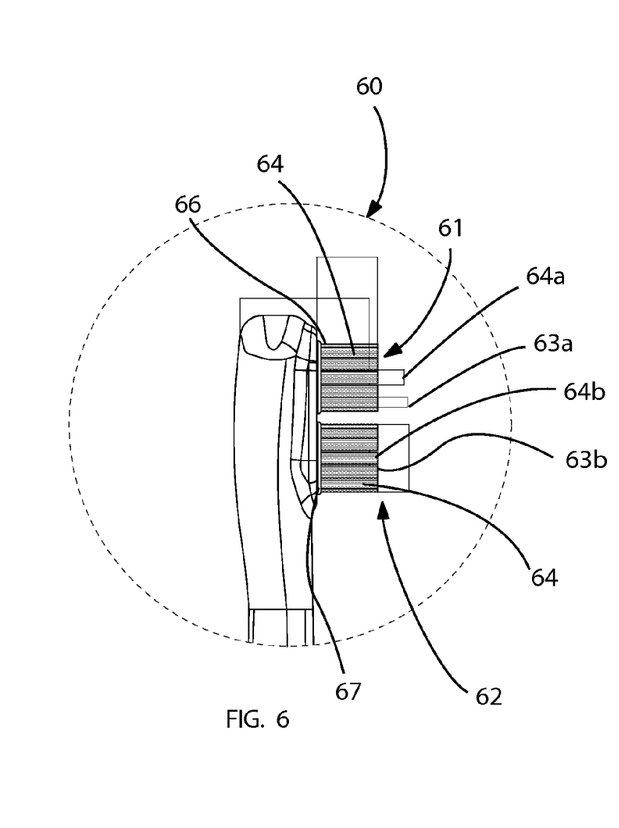
FIG. 6 is a side elevational view of FIG. 5.

Referring to FIGS. 5-6 in particular, polishing brush head 60 may include first and second bristle tuft arrays 61, 62 disposed in a side-by-side configuration. Each bristle tuft array 61, 62 preferably has a plurality of short second bristle tufts 63 and long second bristle tufts 64 concentrically arranged in respective annular configurations. In particular, the long second bristle tufts 63 are arranged in a first circular pattern defined along an outer perimeter of each of the first and second bristle tuft arrays 61, 62 while the short second bristle tufts 64 are arranged concentrically in a second circular pattern spaced inwardly from said long second bristle tufts 63. Each of the first and second bristle tuft arrays 61, 62 may rotate continuously in clockwise and counter clockwise directions to polish more efficiently. For example, while first bristle tuft array 61 rotates continuously in a clockwise direction, second bristle tuft array 62 preferably rotates continuously in a counter clockwise direction. Again, a conventional drive mechanism well known in the art may be employed without departing from the true scope and spirit of the present invention. An exemplary drive mechanism is described hereinbelow but should not be construed as a limiting mechanism for oppositely rotating the first bristle tuft array 61 relative to the second bristle tuft array 62.

Still referring to FIGS. 5-6, the circular and concentric structural configuration of the first and second bristle tuft arrays 61, 62 is important for effectively removing teeth stains. In particular, in each of the first and second bristle tuft array 61, 62, the spatial distance between tips (top of distal ends 63b) of diametrically opposed long second bristle tufts 63 may be approximately 7-8 millimeters. In each of the first and second bristle tuft arrays 61, 62, the spatial distance between tips (top of distal ends 64b) of diametrically opposed short second bristle tufts 64 may be approximately 2-3 millimeters. This allows the short second bristle tufts 64 to effectively access areas on the buccal and lingual surfaces of the teeth while the long second bristle tufts 63 simultaneously access the grooves formed by the proximal surfaces of adjacent teeth in the areas where the proximal teeth contact each other.

As perhaps best shown in FIG. 6, the long second bristle tufts 63 are preferably about 7 millimeters in longitudinal length and have a diameter of approximately 1.5 millimeters at their base 63a. The short second bristle tufts 64 are preferably about 6 millimeters in length and have a diameter of about 2 millimeters at their base 64a. The bristle filaments of both the long bristle tufts 63 and the short bristle tufts 64 may be 0.005 inch in diameter. Each of the first and second bristle tuft arrays 61, 62 may extend upwardly from a circular support plate 66, 67 that measures about 9 millimeters in diameter, for example.

Referring to FIGS. 5-6 and 9, as a non-limiting example, each of the first and second bristle tuft arrays 61, 62 may be driven by a drive mechanism 50, 52 that may include a conventional gear system (not shown) that causes the circular support plate carrying the short and long second bristle tufts 63, 64 of the first bristle tuft array 61 to selectively rotate in a clockwise direction while circular support plate carrying the short and long second bristle tufts 63, 64 of the second bristle tuft array 62 to selectively rotate in a counter clockwise direction. One skilled in the art understands such opposite rotational movements of each of the first and second bristle tuft arrays 61, 62 may be achieved by abutting two rotary gears wherein clockwise rotation of one rotary gear causes counter clockwise rotation of the other rotary gear. Again, such a drive mechanism 50 may encompass a variety of alternate configurations and components and should not be limited to only rotary gears configurations.

As a non-limiting example, the drive mechanism 50 may include a built-in timer to continue the rotary action of the first and second bristle tuft arrays 61, 62 for a predetermined time period such as 2.5 minutes, for example. In particular, the polishing brush head 60 is not intended to brush the teeth with toothpaste, but to gently polish the teeth with a special non-abrasive polishing/whitening cream.

As a non-limiting example, each interchangeable brush head 30, 60 may be color coded. The antimicrobial brush head 30 may be blue and preferably used with the antimicrobial liquigel 35 that matches its color and targets the pathogenic bacteria that live in the mouth. The polishing brush head 60 may be white and preferably used with a tooth polishing/whitening cream 65 to polish and remove stains from the teeth. As an example, the polishing/whitening cream 65 may be pearl white and match the color of polishing brush head 60. The present disclosure advantageously removes bacteria from the teeth/gums for disease prevention and cleans/polishes the teeth/gums for esthetic/cosmetic reasons.

The present invention may further include a method of utilizing an interchangeable toothbrush system for removing microbial masses between teeth and subgingival areas of gums as well as polishing buccal and lingual areas of the teeth. Such a method preferably includes the following chronological steps of cleaning the mouth with the antimicrobial brush head attached to the motorized handle:

1) Place about ½ ounce of the antimicrobial liquigel in the mouth.

2) Place the antimicrobial head brush in the mouth, then turn the brush on.

3) Guide the tips of the long bristle tufts into the spaces between the teeth as you clean each of the spaces between all of the upper and lower teeth.

4) After thoroughly guiding the tips of the long bristle tufts into all of the spaces between all of the teeth, empty the remaining liquigel from the mouth.

5) Rinse the brush head with water and place the brush on the charging base so it will be ready for the next use.

The chronological steps for using the polishing head attached to the motorized handle include:

1) Place a pea-sized portion of polishing/whitening cream on each of the bristle arrays of the polishing brush head.

2) Place the bristles of the polishing brush head on the tooth surfaces you wish to polish.

3) Turn the brush on.

4) Move the bristles of the polishing brush head over the tooth surfaces you wish to polish.

5) After polishing the teeth, rinse the brush head with water and place the brush on the charging base so it will be ready for your next use.

The present invention provides a toothbrush 10 having a handle 11 and a motor drive mechanism 50, 52 situated therein; providing and removably connecting an interchangeable antimicrobial brush head 30 to the handle 11 wherein the antimicrobial brush head 30 has a plurality of first bristle tufts 31, 32 configured in such a manner that the first bristle tufts 31, 32 are capable of accessing microbial masses between the teeth and subgingival areas of the gums; and providing and removably connecting an interchangeable polishing brush head 60 to the handle 11 wherein the polishing brush head 60 has a plurality of second bristle tufts 63, 64 configured in such a manner that the second bristle tufts 63, 64 are capable of polishing buccal and lingual areas of the teeth.

In one embodiment, the antimicrobial brush head preferably includes two distinctly different bristle tuft designs. One of the bristle tuft designs preferably includes a long, narrow diameter configuration that is capable of reaching into areas between teeth where bristles of conventional toothbrushes cannot reach. The individual filaments that form these bristle tufts are slightly stiffer (0.007 inches in diameter) than the filaments in most conventional toothbrushes. This design facilitates entry of the bristle tufts into areas between the teeth and into the spaces between the teeth and gums. This design enables these bristle tips to dislodge and remove bacterial masses that reside in these sites. An important added benefit of this design is that the bristles carry antimicrobial agents into these sites to kill bacteria as the bristle action disrupts the slime layer that normally protects these bacteria from the action of the antimicrobial agents contained in mouth rinses that are swished in the mouth. The long bristle tufts are approximately 10.5 millimeters long and 2 millimeters in diameter. The distal 2.5 millimeters of the bristle tufts are preferably tapered into a cone shape to allow the longest filaments to enter into the narrowest of spaces in the gingival sulcus and interproximal areas.

In one embodiment, the second bristle tuft design preferably includes a shorter, wider diameter configuration with softer individual bristle filaments (0.004 inch in diameter). Softer bristle filaments are advantageous for these bristle tufts because the shorter length of the softer bristles gives them a similar cleaning effectiveness to longer, stiffer bristle filaments and are gentler on the gums than short, stiffer bristles. The purpose of this design is to facilitate disruption and removal of bacterial masses that colonize in the gingival sulcus and on the facial and lingual surfaces of the teeth, and to deliver antimicrobial agents into these areas. The wider diameter of the short bristle tufts enables these tufts to clean the broader areas of the facial and lingual surfaces of teeth. These shorter bristle tufts are preferably 5.5 millimeters in length and 3.5 millimeters in diameter. The distal 2.5 millimeters are preferably tapered to a cone shape to enable the longest of the bristle filaments to enter the gingival sulcus.

The long and short bristle tufts are located in alternating positions on the brush head in parallel rows with approximately 1.25 millimeters between the bristle tufts. The two parallel rows of bristle tufts are spaced with 3.5 millimeters between the wide diameter tufts and 4 millimeters between the narrow diameter tufts. There is an 8 millimeter distance between the axis of rotation between both the long and short bristle tufts. This allows the long, narrow bristle tufts to reach into the areas between the teeth while the short bristle tufts clean the facial and lingual surfaces. Most toothbrush designs have the bristle tufts placed too close together. This causes the bristles to crowd each other out of the narrow interproximal spaces and prevent entry of the bristle filaments into areas occupied by harmful bacteria. Thus, the bristles of conventional toothbrushes cannot enter into these tiny spaces to remove bacteria that live in those spaces. These are the very bacteria that cause much of the tooth decay and periodontal disease that most people experience.

Each bristle tuft preferably rotates back and forth in a reciprocating movement approximately 1.25 turns in each direction around its long axis. This reciprocating action is important to the effective function of this antimicrobial brush design. It propels the bristle tips deep into the interproximal and the gingival sulcus areas. A rotating motion in one direction would cause the bristles to "run out" of these narrow areas and not enable the bristle tips to enter as deep into these areas. The mechanism that drives the bristle tufts of this invention consists of a rack and gear system. The rack and gear drive system has been used in the prior art of electric toothbrush design.

Figure 10:
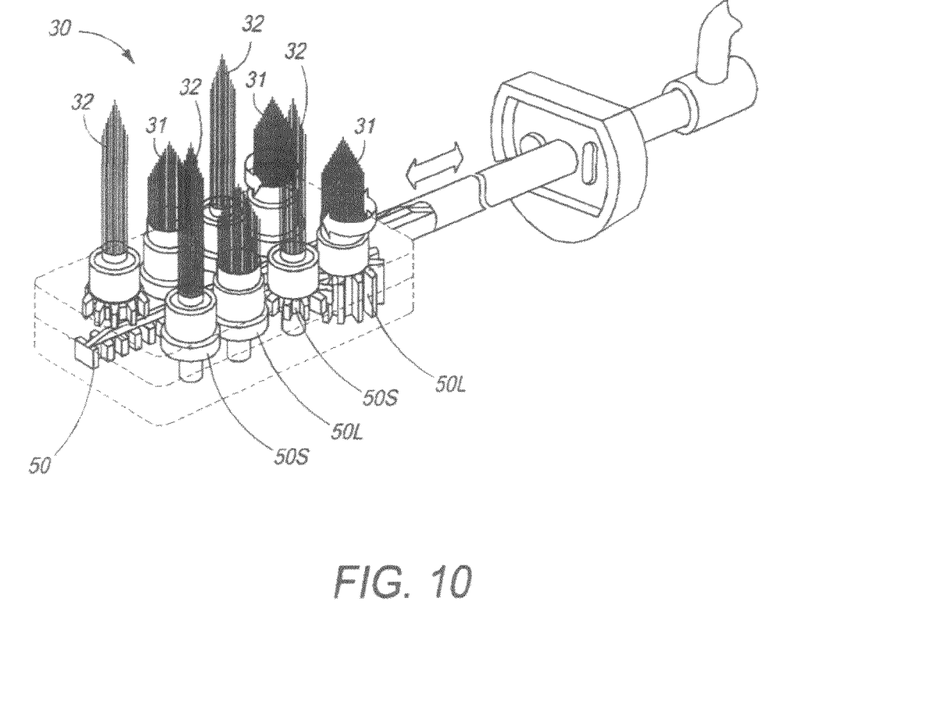
FIG. 10 is a side view depicting the long and short bristled tufts driven by a rack and gear system.

The invention is different from the prior art in the unique bristle tuft designs and in its unique method of use as described above. The rack 50R and gear 50S and 50L drive system 50 used in previous embodiments of the art has not maintained a significant market share. Nor have toothbrushes incorporating this drive system been included in recent research in the art and science of contemporary oral hygiene. Toothbrushes with this drive system are generally not found in retail outlets that sell oral hygiene products and devices.

The March 2010 issue of Consumer Reports published ratings of 10 electric toothbrushes. None of the toothbrushes tested are capable of reaching between the teeth adequately because of their bristle action and tuft design. None are driven by the rack and gear drive system. This appears to be because, when toothbrushes driven by a rack and gear system are used with toothpaste, the polishing grit from the toothpaste gets into the rack and gear system. The polishing grit creates sufficient friction that it causes the bristle movement to stop when pressure is applied to the bristles as the brush is used. Also, if the brush head is not meticulously cleaned, the toothpaste will dry in the rack and gear system causing it to "freeze" and the brush head will be ruined. It is for these reasons, that this invention should never be used with toothpaste. In addition, the benefit to the user in preventing dental diseases is much greater when it is used with an antimicrobial agent rather than toothpaste.

In one embodiment, the second brush head has been designed to be used for cleaning and polishing the tooth surfaces. It can be attached to the same motorized handle that powers the previously described antimicrobial brush head. It consists of two arrays of bristle tufts each 9 millimeters in diameter. These arrays of bristle tufts rotate continuously in opposite directions. The arrays of bristle tufts consist of four 2 mm diameter bristle tufts with approximately 6 mm long filaments located in the central portion of the rotating disk that carries them. These tufts are encircled by twelve approximately 1.5 mm diameter bristle tufts that are approximately 7 mm long. This arrangement of the bristle tufts forms a shallow cup-like arrangement. This shape allows the longer outside bristle tufts to polish in the groove areas where adjacent teeth contact each other. The shorter inner bristle tufts polish the broader, flatter facial and lingual surfaces of the teeth. This brush head is to be used with a polishing/whitening cream containing a polishing compound that is non-abrasive. The system that drives the rotating bristle arrays may be a simple direct drive gear system, well known in the industry.

In the embodiment, the antimicrobial brush head may include long, narrow bristles driven in an oscillating motion rotating on their long axis can enter into areas that no other brush on the market can reach. This allows bristle filaments to enter these areas to remove bacteria from and carry antimicrobial agents into these areas. Short, wider diameter tufts of softer bristles driven in an oscillating motion rotating on their long axis remove bacteria from the facial and lingual surfaces with less possibility of irritating gingival tissues. Bristle tuft spacing allows the bristles to enter creases and crevices without being "crowded out" by bristles from adjacent tufts. The small size of the creases and crevices in interproximal and gingival sulcus areas allows a limited number of bristle tufts to enter these tiny spaces.

Long and short bristle tufts in alternating positions prevents adjacent bristles from "crowding" each other out of tiny spaces. This allows bristle filaments to enter these areas to remove bacteria and carry antimicrobial agents into these areas. The greater difference in length (approximately 5 mm) between the long and short bristles prevents long and short bristles from "crowding" each other out of tiny spaces.

In one embodiment, the polishing brush head may include dual bristle arrays continuously rotating in opposite directions. This enables bristle filaments to brush both sides of the grooves formed by teeth adjacent to each other. Dual bristle arrays rotating continuously without reversing results in more efficient polishing. This movement is similar to polishing instruments used by dental hygienists. Because the teeth are fixed in place and cannot be moved while being polished, the position of the polishing device must be able to be maneuvered to conform to the shapes of the teeth. The soft bristle filaments avoid abrasion to gingival tissues.

Bristle tufts arranged with shorter tufts in the central portion and longer bristle tufts located around periphery to form a cup-like configuration. This arrangement allows bristle tufts around periphery of the rotating bristle arrays to enter grooves formed by the shapes of adjacent teeth for more effective polishing. Side by side rotating bristle arrays tend to stabilize the brush head against running along teeth. This feature gives the operator better control. As noted hereinabove, the brush heads of the present invention should not be used with toothpastes that are highly abrasive.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention. In particular, with respect to the above description, it is to be realized that the optimum dimensional relationships for the parts of the present invention may include variations in size, materials, shape, form, function and manner of operation.

What is claimed is:

1. A toothbrush head attachment equipped with a combination of bristled tufts which when operationally driven by a power source and a complete brushing of tooth surfaces including interproximal tooth surfaces and subgingival areas therewith serves to effectively dislodge bacteria of a biofilm adhering about the tooth surfaces allowing for an effective antimicrobial agent treatment thereof to kill the dislodged bacteria and-thereby provide the tooth surfaces substantially free from surviving bacteria; said attachment comprising a drive system equipped to counterrotate adjacently positioned bristled tufts of the combination about a central tuft axis for each of the bristled tufts, said combination of bristled tufts being characterized as comprising a plurality of short bristled brush tufts and a plurality of long bristled brush tufts positioned in an alternating sequence of said short bristled tufts and said long bristled tufts in a paired rowed arrangement of a first row arrangement with a second row arrangement having a sequential mating of said long bristled tufts and said short bristled tufts such that each sequence of the short bristled tufts and the long bristle tufts in the first row arrangement and the second row arrangement will laterally and sequentially mate with each other, said long bristled brush tufts being further characterized as having a substantially longer and narrower tuft size than the short bristled tufts, with the long bristled tufts being comprised of bristled filaments of a sufficient length, sufficient cross-sectional dimensional stiffness and a sufficient number of the long bristled filaments of a tuft cross-sectional size so as to enable the long bristled brush tufts upon operational use to independently penetrate onto and dislodge the biofilm from the interproximal tooth surfaces and the subgingival areas, said short bristled brush tufts being characterized as being comprised of a number of short bristled filaments of a substantially softer and shorter filament structure than the long bristled filaments, with said short tuft bristled tufts providing a sufficient cross dimensional tuft size and a filament structure to operationally permit the short bristled tufts to dislodge the bacteria of the biofilm about facial tooth surfaces and lingual tooth surfaces while also providing sufficient spacing between adjacently positioned long bristled brush tufts to permit the long bristled tufts upon operational use to independently penetrate onto the interproximal tooth surfaces and the subgingival areas and thereby dislodge the bacteria therefrom so as to permit the effective antimicrobial agent treatment thereof.

2. The attachment according to claim 1 wherein the drive system for driving the bristled tufts is preset at a reciprocating rotational rate so as to facilitate the long bristled tufts to independently penetrate onto the interproximal tooth surfaces and the subgingival areas and the-bristled tufts of the first row arrangement and the second row arrangement are in parallel alignment and spaced apart at a lateral distance ranging from about 3 to 4 millimeters.

3. The attachment according to claim 1 wherein the drive system for driving the bristled tufts is preset at a reciprocating rotational rate so as to facilitate the long bristled tufts to independently penetrate onto the interproximal tooth surfaces and the subgingival areas and the power source for driving a rack and gear system comprises a rechargeable battery powered motor.

4. The attachment according to claim 1 wherein the drive system comprises a rack and gear drive system preset to reciprocally rotate and counter rotate the bristled tufts at a rotational rate so as to maintain upon operational use thereof structural integrity of the long bristled tufts and thereby enable the long bristled tufts to independently penetrate onto the interproximal tooth surfaces and the subgingival areas and thereby in cooperation with the short bristled tufts serve to effectively dislodge the bacteria of the biofilm from the tooth surfaces to provide the tooth surfaces characterized upon the antimicrobial agent treatment thereof as having no more than a miniscule level of surviving bacteria.

5. The attachment according to claim 4 wherein upon operational use the short bristled brush tufts provide the sufficient cross-sectional size and the filament length to effectively dislodge the biofilm from, the facial surfaces and lingual surfaces of the teeth while also providing sufficient lateral spacing apart from the long bristled tufts to allow the long bristled tufts to independently penetrate onto the interproximal tooth surfaces and the subgingival areas and the short bristled filaments are further characterized as having a smaller filament diameter than the long bristled filaments.

6. The attachment according to claim 4 wherein the long bristled tufts are terminated by a cone shaped tip.

7. The attachment according to claim 6 wherein the cross-sectional size of the short bristled tufts is substantially greater in size than the cross-sectional size of the long bristled tufts and the power source comprises a rechargeable battery powered motor.

8. The attachment according to claim 7 wherein the lateral distance between the cone shaped tip of the long bristled tufts in each row of the paired rowed arrangement measures about 8 millimeters apart and the first row arrangement and the mating second row arrangement each contain the combination of four bristled tufts.

9. The attachment according to claim 4 wherein the first rowed arrangement and the second row arrangement are in parallel alignment and each row contains four bristled tufts and the central tuft axis of rotation of the short bristled tufts in each row of the paired arrangement measures at about 8 millimeters.

10. A method for effectively dislodging a biofilm from tooth surfaces including interproximal areas and subgingival areas with a toothbrush head attachment equipped with a combination of bristled tufts which when operationally driven by a power source and a complete brushing of tooth surfaces including interproximal tooth surfaces and subgingival areas therewith serves to effectively dislodge bacteria of a biofilm adhering about the tooth surfaces so as to allow for an effective antimicrobial agent treatment thereof, said method comprising:

A) providing the brush head attachment comprising the combination of the bristled tufts driven by a drive system equipped to counterrotate adjacently positioned bristled tufts of the combination about a central tuft axis for each of the bristled tufts; said combination of bristled tufts being characterized as comprising a plurality of short bristled brush tufts and a plurality of long bristled brush tufts arranged in an alternating sequence of the short bristled tufts and the long bristled tufts in a paired rowed arrangement of a first row arrangement with a second row arrangement such that each sequence of the short bristled tufts and the long bristled tufts in the first row arrangement and the second row arrangement will laterally and sequentially mate with each other, said long bristled brush tufts being further characterized as having a substantially longer and narrower tuft size than the short bristled tufts with the long bristled tufts being comprised of long filaments of a sufficient length, sufficient cross-sectional dimensional stiffness and sufficient number of the long filaments to permit the long bristled brush tufts upon operational use to independently penetrate onto and dislodge the biofilm from the interproximal tooth surfaces and the subgingival areas with said short bristled brush tufts being characterized as being comprised of short bristled filaments of a substantially softer and shorter filament structure than the long filaments with said short bristled tufts providing a sufficient cross-sectional dimensional tuft size and a filament structure to operationally permit the short bristled tufts to dislodge the biofilm about facial tooth surfaces and lingual tooth surfaces while also providing sufficient spacing between adjacently positioned long bristled brush tufts to permit the long bristled tufts upon the operational use to independently penetrate onto the interproximal tooth surfaces and the subgingival area and thereby dislodge the bacteria therefrom so as to permit the effective antimicrobial agent treatment thereof; and a power driven brush head tuft drive system equipped to rotationally turn each of the adjacently positioned bristled tufts about a central rotational axis in sequenced, reciprocating and opposing tuft rotational directions;

B) equipping said toothbrush head attachment with the power source; and

C) operationally powering the drive system of the brush head attachment while effectively engaging the bristled tufts onto essentially all of the tooth surfaces including the interproximal tooth surfaces, the subgingival areas, the facial surfaces, and the lingual tooth surfaces to effectively dislodge the biofilm and expose the bacteria therewithin and thereby permit for the effective antimicrobial agent treatment thereof.

11. The method according to claim 10 wherein method includes treating the dislodged bacteria with an antimicrobial agent so as to thereby kill and reduce the bacteria to the miniscule level and the drive system for driving the bristle tufts is preset at a reciprocating rotational rate so as to facilitate the long bristled tufts to independently penetrate onto the interproximal tooth surfaces and the subgingival areas.

12. The method according to claim 11 wherein the effective antimicrobial agent treatment comprises treating the dislodged bacteria with an antimicrobial agent in a gelled liquid form applied during the operational powering of the head attachment and the power source comprises a rechargeable battery powered motor.

13. The method according to claim 11 wherein the short bristled brush tufts provide sufficient cross-sectional size and filament length to effectively dislodge the bacteria of the biofilm about the facial tooth surfaces and the lingual tooth surfaces while also providing in combination with the long bristled tufts sufficient spacing to enable a complete brushing of all the tooth surfaces and permit effective penetration of the long bristled tufts onto the interproximal tooth surfaces and the subgingival areas without interference to the penetration by the short bristled tufts.

14. The method according to claim 10 wherein drive system comprises a rack and gear mechanism for operationally driving individually each of the bristled tufts about the central axis for each of the bristle tufts in the sequenced reciprocating and opposing rotational directions of the adjacently bristled tufts with said rack and gear system being preset at a rotational speed and a reciprocating rate so as to maintain structural integrity of the long bristled tufts for the effective penetration onto the interproximal surfaces and the subgingival areas and the power source comprises a rechargeable battery powered motor.

15. The method according to claim 14 wherein the first row arrangement and the second row arrangement are laterally spaced at about 3 to about 4 millimeters apart.

16. The method according to claim 15 wherein the long bristled tufts are characterized as having a cone shaped tip.

17. The method according to claim 10 wherein the drive system for driving the bristled tufts is preset at a reciprocating rotational rate so as to facilitate the long bristled tufts to independently penetrate onto the interproximal tooth surfaces and the subgingival areas and a complete brushing of the tooth surface is effectuated by operatively engaging the bristled tufts so as to make contact upon all of the tooth surfaces so as to thereby dislodge essentially all of the biofilm and expose the bacteria to the effective antimicrobial agent treatment.

18. The method according to claim 17 wherein the treating of the bacteria with the antimicrobial agent is conducted simultaneously while operationally dislodging the biofilm from the tooth surfaces with said combination of bristle tufts.

19. The method according to claim 18 wherein the treating includes treating the dislodged bacteria with the antimicrobial agent in the form of a gelled liquid.

20. The method according to claim 19 wherein the drive mechanism consists essentially of a rack and gear drive system driven by a rechargeable battery powered motor preset to reciprocally rotate and counter rotate the bristled tufts at a rotational rate so as to maintain upon operational use thereof structural integrity of the long bristled tufts and thereby permit the long bristled tufts to independently penetrate onto the interproximal tooth surfaces and the subgingival areas and thereby in cooperation with short bristled tufts serve to effectively dislodge the biofilm from essentially all of the tooth surfaces.

* * * * *